US012181440B2

(12) United States Patent
Giese et al.

(10) Patent No.: US 12,181,440 B2
(45) Date of Patent: Dec. 31, 2024

(54) NITROGEN-DRIVEN DESORPTION BY A DIAZIRINE

(71) Applicant: Northeastern University, Boston, MA (US)

(72) Inventors: Roger W. Giese, Hanover, MA (US); Pushkar Kulkarni, Allston, MA (US)

(73) Assignee: Northeastern University, Boston, MA (US)

( * ) Notice: Subject to any disclaimer, the term of this patent is extended or adjusted under 35 U.S.C. 154(b) by 335 days.

(21) Appl. No.: 17/881,943

(22) Filed: Aug. 5, 2022

(65) Prior Publication Data

US 2023/0067189 A1 Mar. 2, 2023

Related U.S. Application Data

(60) Provisional application No. 63/230,437, filed on Aug. 6, 2021.

(51) Int. Cl.
*G01N 27/64* (2006.01)
*G01N 33/68* (2006.01)
*H01J 49/00* (2006.01)

(52) U.S. Cl.
CPC ......... *G01N 27/64* (2013.01); *G01N 33/6851* (2013.01); *H01J 49/0027* (2013.01)

(58) Field of Classification Search
CPC .............. G01N 27/64; G01N 33/6851; G01N 33/6848; H01J 49/0027

USPC ........................................ 250/281, 282, 288
See application file for complete search history.

(56) References Cited

FOREIGN PATENT DOCUMENTS

WO WO-2020/237132 A1 11/2020

OTHER PUBLICATIONS

Ziemianowicz, et al ("Amino Acid Insertion Frequencies Arising from Photoproducts Generated Using Aliphatic Diazirines," J. Am. Soc. Mass Spectrom. (2017) 28:2011-2021 (Year: 2017).*
Ziemianowicz et al., "Amino Acid Insertion Frequencies Arising from Photoproducts Generated Using Aliphatic Diazirines", Journal of American Society for Mass Spectrometry 28: 2011-2021 (2017).

* cited by examiner

*Primary Examiner* — Michael Maskell
(74) *Attorney, Agent, or Firm* — Foley Hoag LLP; Dana M. Gordon; Laura A. Wzorek

(57) ABSTRACT

Disclosed is a method of desorbing an adsorbed material by subjecting to energy a diazirine adsorbed on a solid surface or a layer on the solid surface, which causes the diazirine to form a carbene and nitrogen gas; and using the energy of the resultant nitrogen gas to desorb the adsorbed material from the solid surface or a layer on the same. Also disclosed is a method of reacting the resultant carbene with (a) a material in the gas phase proximal to the first solid surface; (b) a material adsorbed on a second solid surface proximal to the first solid surface; or (c) a second solid surface proximal to the first solid surface.

20 Claims, 4 Drawing Sheets

NITROGEN-DRIVEN DESORPTION BY A DIAZIRINE

RELATED APPLICATION

This application claims the benefit of priority to U.S. Provisional Patent Application No. 63/230,437, filed Aug. 6, 2021.

BACKGROUND OF THE INVENTION

A diazirine can be activated to a corresponding carbene with liberation of a molecule of nitrogen by energy, such as UV radiation or heat. A carbene typically is highly reactive in various ways including insertion into the bond of a nearby molecule on the order of low nanoseconds. Among the uses of diazirines are diazirine-substituted ligands to probe the binding site of a binding partner such as a protein, to conduct a footprinting experiment, and to crosslink a polymer by using a bis-diazirine. These applications rely on the reactivity of the carbene resulting from activation of the diazirine. For example, in a diazirine footprinting (molecular painting) experiment, one can learn which parts of a substance or complex of interest are most exposed, since these parts will tend to react preferentially with the diazirine-derived carbene.

Matrix-Assisted Laser Desorption Ionization Mass Spectrometry (MALDI-MS) is a common form of mass spectrometry in which a sample usually starts out as a spot on a metal plate (F. Hillenkamp, and J. Peter-Katalinic, eds, MALDI MS, Wiley-VCH Verlag GMBH and Co., KGaA, Weinheim, 2007). The spot comprises a photon-absorbing material referred to as the matrix, and also one or more analyte molecules which are entrained in this matrix. Subjecting the spot to a pulse or multiple pulses of laser photons desorbs the matrix molecules into the gas phase above the spot, which usually is a vacuum. This is because the matrix molecules absorb the energy-rich photons, and thereby explode vibrationally off the surface. Analyte molecules entrained in the matrix are swept up in this desorption process, initially as clusters with matrix molecules, and may acquire a charge (if they don't have one already) as by combining with a proton. Such analyte molecules are therefore considered to be "secondarily desorbed". Charged analyte molecules in this plume are then resolved and detected in other parts of the mass spectrometer. In a related technique, gas phase charged analyte molecules from desorption are detected by ion mobility spectrometry instead of mass spectrometry.

While MALDI-MS earned a Nobel Prize and is widely used, it has some major disadvantages. First of all, many small analytes lack a charge and do not acquire one during the desorption event, so they fall out of the scope of MALDI-MS. Second, there are many options for matrices, along with many recipes for using them, and much time and cost can go into finding the right matrix, the right concentration, and the right deposition technique to get a good result. Third, the matrices usually are small organic compounds, which tend to give many background peaks in the MALDI-MS spectrum in the low mass range, some of which can occlude detection of a small analyte of interest. This problem is compounded since much matrix needs to be present to adequately entrain the analytes and protect them from direct high laser energy exposure. Fourth, a spot may be non-uniform, for example, when the matrix crystallizes non-uniformly, and the MALDI performance usually depends on the details of the zone that is irradiated. The signal from an analyte therefore usually varies from one position to another in the spot. Fifth, analytes can compete for the protons, and the number of protons is limited, so only some analytes may be detected with good sensitivity. Sixth, common matrices must be crystallized in the spot to work effectively, but a high level of contaminants or sample can prevent effective crystallization. Seventh, the best matrix for a given sample may be expensive, precluding its general use. Eighth, it is difficult to obtain quantitative results without a stable isotope internal standard, but too much internal standard can cause ion suppression. Overall, the MALDI part of MALDI-MS is delicate and compromised in many ways, especially for detection of small molecules.

MALDI plates, which provide a solid surface, most often are stainless steel. However, gold-coated glass plates and indium tin oxide (ITO)-coated glass plates are also employed, especially for tissue imaging, since they are electrically conductive (like stainless steel, so they don't build up a charge that interferes with MALDI), and also transparent (so the deposited tissue sample can also be evaluated by light microscopy). The gold and ITO surfaces can be covalently modified. For gold, this is commonly accomplished by chemisorption or physisorption of a thiol reagent. For an ITO surface, commonly this is done by covalent silanization with a trichlorosilyl- or trialkoxysilyl-substituted reagent.

In SALDI (surface-assisted laser desorption ionization) mass spectrometry, inorganic particles or inorganic porous surfaces are used as the substrate (target) of the laser photons rather than an organic matrix substrate as in MALDI. SALDI has been reviewed (Muller, W. H., Verdin, A., De Pauw, E. Dd., Malherbe, C., Eppe, G. [2022] Surface-assisted laser desorption/ionization mass spectrometry imaging: A review. Mass Spec. Rev. 41, 373-420). SALDI is not used much since it has one or more of the following disadvantages: impractical, delicate, tedious, analyte-dependent, and expensive.

Laser desorption mass spectrometry, where there is no matrix, preceded MALDI-MS, but was not successful since the desorption was inefficient. This problem was overcome by MALDI-MS, but with many new problems, as summarized above. MALDI-MS is a form of laser desorption MS.

Various types of thin porous films can be formed on solid surfaces, such as covalent organic films (Cote, A. P., Benin, A. I., Ockwig, N. W., O'Keeffe, M. O., Matzger, A. J., Yaghi, O. M. [2005] Porous, Crystalline, Covalent Organic Frameworks. Science 310, 1166-1170); polymer nanobrushes (Schilp, S., Ballav, N., Zharnikov, M. [2008] Fabrication of a Full-Coverage Polymer Nanobrush on an Electron-Beam-Activated Template. Angew. Chem. Int. Ed. 47, 6786-6789), polymeric organics, metal-organic frameworks (MOFs), porous silicas, nanowires, sol-gels, gels, and zeolites.

Atomic force microscopy is a useful technique for imaging substances including molecules on a solid surface under liquid as well as gaseous conditions, as has been reviewed especially for DNA samples (Main, K. H., Provan, J. L., Haynes, P. J., Wells, G., Hartley, J. A., and Pyne, A. L., Atomic force microscopy-A tool for structural and translational DNA research, APL Bioengineering 5, 036101 [2021] https://doi.org/10.1063/5.0054984). However, taking advantage of the method to achieve covalent modification of a material being examined is unknown.

Diazomethane, a gaseous substance, has been chemisorbed onto a Pd(1,10) surface, and heated to release its methylene and nitrogen components into the gas phase, and the released methylene was detected by mass spectrometry (Serghini Monim, S. and McBreen, P. H. [1992] Ejection of CH$_2$ from Adsorbed CH$_2$N$_2$ into the Gas Phase, J. Phys. Chem., 96, 2704-2707). It was considered that the CH$_2$ group was ejected directly from CH$_2$N$_2$. There was no consideration of nitrogen-driven desorption, detection, motion, or synthesis of another material, and the desorbed carbene was not reported to react with any material; it was simply detected.

A cationic mass tag with a diazirine moiety (CAX-DZ) has been employed for detection purposes where a dissolved sample containing this reagent and analyte is subjected to LED photons or heat to give a corresponding carbene that labels the analyte (Kulkarni, P., Giese, R. W., Wang, P. Carbene Mass Tagging, International Patent Application WO 2020/237132, November 2020 (26.11.2020). Detection is done after subsequent processing steps by mass spectrometry or ion mobility spectrometry. This process did not involve desorption driven by nitrogen.

Conversion of a diazirine to a carbene and nitrogen within a solid is known. For example, a diazirine in frozen water was photoactivated to a carbene and nitrogen (Ziemianowicz, D. S., Bomgarden, R., Etienne, C., Schriemer, D. S., Amino Acid Insertion Frequences Arising from Photoproducts Generated Using Aliphatic Diazirines, J. Am Soc. Mass Spectrom. [2017] 28: 2011-2021.) This work was done to evaluate diazirines for footprinting studies. This process did not involve desorption.

SUMMARY OF THE INVENTION

In certain aspects, the present invention provides methods of desorbing an adsorbed material, comprising the steps of:
(i) providing a solid comprising a first solid surface on which a diazirine and a material are adsorbed;
(ii) exposing the diazirine to a source of energy, thereby generating a carbene and nitrogen gas;
wherein the nitrogen gas evolves from the first solid surface with sufficient energy to desorb the material from the first solid surface.

In further aspects, the present invention provides methods of reacting a carbene, comprising the steps of:
(i) providing a solid comprising a first solid surface on which a diazirine is adsorbed;
(ii) exposing the diazirine to a source of energy, thereby generating a carbene and nitrogen gas;
wherein the nitrogen gas evolves from the first solid surface with sufficient energy to desorb the carbene from the first solid surface; and
(iii) reacting the desorbed carbene with one of:
  (a) a material in the gas phase proximal to the first solid surface;
  (b) a material adsorbed on a second solid surface proximal to the first solid surface, wherein the second solid surface is comprised by the solid or a second solid; or
  (c) a second solid surface proximal to the first solid surface, wherein the second solid surface is comprised by the solid or a second solid.

DETAILED DESCRIPTION OF THE INVENTION

Figure 1:
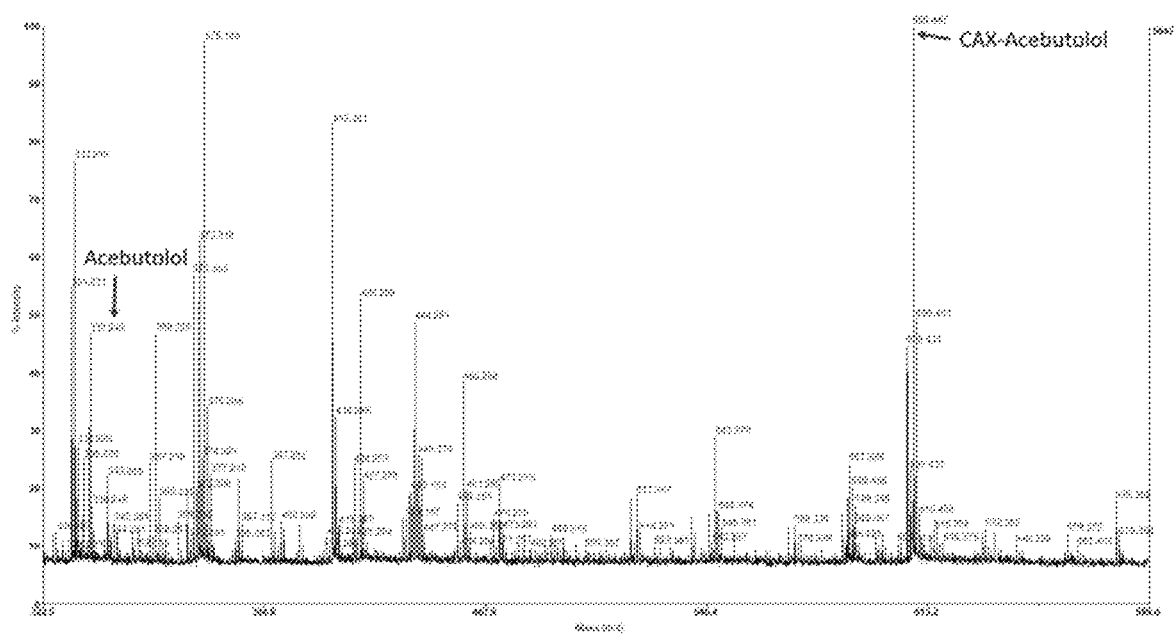
FIG. 1 shows the detection of acebutolol in both a free and labeled form by N$_2$-Driven Desorption Mass Spectrometry (N2D2-MS).
Figure 2:
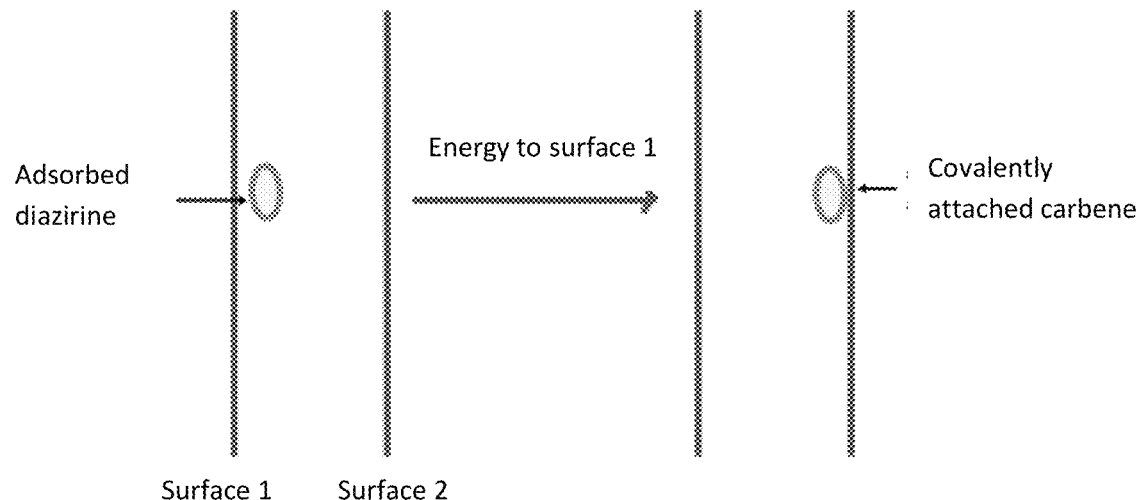
FIG. 2 shows a concept for carbene painting or printing by N2D2.
Figure 3:
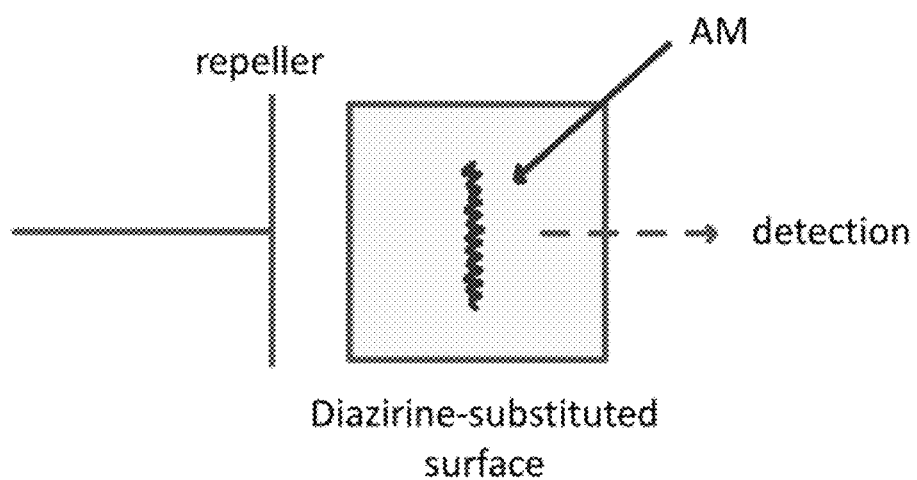
FIG. 3 shows a concept for solid phase orthogonal time-of-flight mass spectrometry (oTOF-MS) detection of adsorbed material (AM) where nitrogen from a nongaseous diazirine on the surface after a laser pulse desorbs the AM up (towards the reader), in front of the repeller. For example, if AM is a protein that desorbs as a neutral, turning on the voltage of the repeller removes a counterion from the protein, giving the protein a charge so it goes to the detector.
Figure 4:
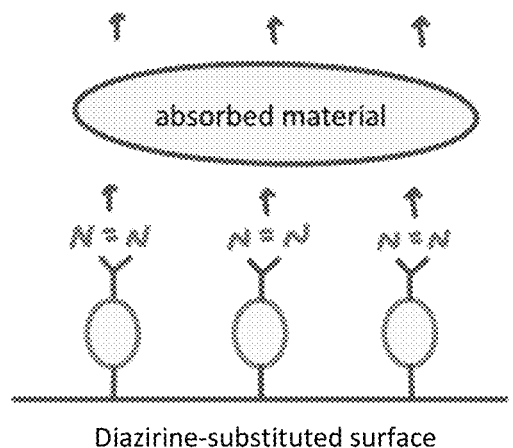
FIG. 4 shows a concept for nitrogen-driven desorption of adsorbed material, wherein the material initially is on or in a layer of diazirine attached covalently to a solid surface, and then application of energy creates nitrogen gas that, in turn, desorbs the adsorbed material (shown in flight) for detection.
Figure 5:
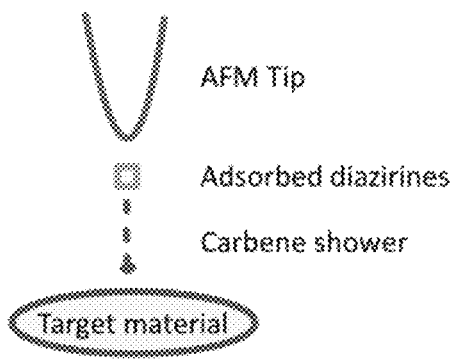
FIG. 5 shows a concept for Covalent Modification Atomic Force Microscopy based on N2D2. Adsorbed diazirine on the AFM tip yield a carbene shower to modify the target material.

Surprisingly, the inventors discovered that the nitrogen gas released during energetic activation of a diazirine on a solid support can be harnessed and used to desorb one or more materials from the solid surface, either intact or in a form labeled by the carbene formed by activation of the diazirine. Thus, the present invention provides methods of desorbing a material from a solid surface. The present invention also provides methods of reacting a carbene generated from activation of a diazirine on a solid surface.

Definitions

As used herein, the term "$C_{x-y}$", when used in conjunction with a chemical moiety, such as, acyl, acyloxy, alkyl, alkenyl, alkynyl, or alkoxy is meant to include groups that contain from x to y carbons in the chain. A $C_{1-6}$ alkyl group, for example, contains from one to six carbon atoms in the chain.

As used herein, the term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "aryl" as used herein include substituted or unsubstituted single-ring aromatic groups in which each atom of the ring is carbon. For example, the ring is a 6- to 10-membered ring, such as a 6-membered ring. The term "aryl" also includes polycyclic ring systems having two or more cyclic rings in which two or more carbons are common to two adjoining rings wherein at least one of the rings is aromatic, e.g., the other rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "diazirine", is art-recognized and may be represented by the general formula

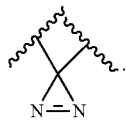

The term "carbene", is a molecule containing a neutral carbon atom with a valence of two and two unshared valence electrons. A carbene may be represented by the general formula

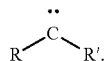

The terms "halo" and "halogen" ("Hal") as used herein means halogen, and includes chloro, fluoro, bromo, and iodo.

The term "polyhalogenated hydrocarbon", as used herein, relates to a hydrocarbon, such as an alkane, an alkene, an alkyne, or an arene, in which multiple hydrogen atoms are replaced with halogens. For example, a polyhalogenated hydrocarbon can be polyfluorinated (multiple hydrogen atoms are replaced with fluorines), polychlorinated (multiple hydrogen atoms are replaced with chlorines), or polybrominated (multiple hydrogen atoms are replaced with bromines).

The terms "heteroaryl" includes substituted or unsubstituted aromatic single ring structures, whose ring includes at least one heteroatom (such as O, N, or S). A heteroaryl can contain one or multiple heteroatoms, for example, one to four heteroatoms, such as one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocycles. Heteroaryl groups include, for example, pyrrole, furan, thiophene, imidazole, oxazole, thiazole, pyrazole, pyridine, pyrazine, pyridazine, pyrimidine, and the like.

The term "layer" as used herein means a liquid or solid film, e.g., on a solid surface, which film may be porous or nonporous; hard or soft; may comprise dissolved or undissolved material internally or on its exposed surface; and be bonded covalently or may be non-covalently bound to the underlying solid surface.

The term "material" indicates a substance including, e.g., drugs, drug metabolites, biomolecules, radicals, ions, salts, sugars, metabolites, peptides, organic reagents, proteins, glycoproteins, nucleic acids, nucleic acid monomers, DNA adducts, phages, natural products, pesticides, pollutants, surfactants, solvents, sugars, lipids, liposomes, exosomes, vesicles, glycans, ribosomes, nanoparticles, viruses, organelles, chromosomes, bacteria, cells, or particles, Preferably the material does not comprise a diazirine moiety.

The term "solid surface" means a non-dissolved bulk surface, which may be particulate or non-particulate, where the latter may be suspended in a gas, or located on a non-particulate solid surface in or on a layer thereon.

The term "spot" as used herein means a zone comprising liquid, solid, or a mixture of liquid/solid material on a solid surface. In some embodiments, the spot is a small layer.

The term "adsorbed" indicates a material covalently or non-covalently adhered to a solid surface or layer on the solid surface. Adsorbed also encompasses a material adhered to a surface by dissolving in a liquid layer.

The term "desorb" or "desorption" means departure of an adsorbed material from a solid surface, or from a layer on a solid surface into a gas or liquid phase. Desorbing may occur under vacuum conditions. In some embodiments, desorption encompasses desorbing a carbene (e.g., into the gas phase) from a nongaseous adsorbed diazirine on a solid surface.

In certain embodiments, the invention provides a method of desorbing an adsorbed material, comprising the steps of:
(i) providing a solid comprising a first solid surface on which a diazirine and a material are adsorbed;
(ii) exposing the diazirine to a source of energy, thereby generating a carbene and nitrogen gas;
wherein the nitrogen gas evolves from the first solid surface with sufficient energy to desorb the material from the first solid surface.

In certain embodiments, the diazirine and the material are comprised in a single layer adsorbed on the first solid surface. In certain such embodiments, the diazirine and the material are homogeneously distributed in the single layer. In alternative embodiments, the diazirine and the material are heterogeneously distributed in the single layer.

In certain embodiments, the diazirine is comprised in a first layer adsorbed on the first solid surface, and the material is comprised in a second layer adsorbed on the surface of the first layer.

In certain embodiments, the diazirine is covalently bound to the first solid surface.

In other embodiments, the diazirine is covalently bound to the single layer adsorbed on the first solid surface, or to the first layer adsorbed on the first solid surface.

In certain embodiments, the carbene is not desorbed from the first solid surface.

In other embodiments, the diazirine is not covalently bound to the first solid surface.

In certain embodiments, the carbene is desorbed from the first solid surface. In certain such embodiments, the carbene is substantially inert.

In further embodiments, the carbene reacts with the material to form a labeled material. In certain such embodiments, the carbene reacts with the material to form a labeled material in the gas phase after the material is desorbed from the first solid surface. In other such embodiments, the carbene reacts with the material to form a labeled material before the material is desorbed from the first solid surface.

In certain embodiments, the source of energy is selected from the group consisting of UV photons, LED photons, UV LED photons, heat, laser photons, electrons, photons from fluorescence energy transfer, plasma, a metastable compound, an energy-releasing molecule, a vibrationally-activated molecule, and a combination thereof. The energy-releasing molecule may be, for example, ozone, an ozonide, or a peroxide. In some preferred embodiments, the source of energy is heat, a laser photon, or an LED photon.

In certain embodiments, the method further comprises analyzing the desorbed material. Analyzing the desorbed material may include, for example, analyzing the desorbed material by an analytical method selected from the group consisting of ion mobility spectrometry, mass spectrometry, liquid chromatography-electrospray ionization mass spectrometry, infusion-electrospray ionization mass spectrometry, laser desorption mass spectrometry, and matrix-assisted laser desorption ionization mass spectrometry. In preferred embodiments, the analytical method is ion mobility spectrometry, mass spectrometry, or laser desorption mass spectrometry; most preferable is laser desorption mass spectrometry.

In certain embodiments, the desorbed material reacts with a reagent. Such reaction can occur, for example, in the gas phase. In certain embodiments, the reagent is bound to or adsorbed on a second solid surface, wherein the second solid surface is comprised by the solid or a second solid, and the desorbed material reacts with a reagent on the second solid surface. In certain embodiments, the reaction of the desorbed material with a reagent covalently modifies the material, e.g., to make the material more detectable by one or more analytical methods, or to make the material more useful for a particular application.

In certain embodiments, the diazirine comprises a quaternary amine associated with a counterion, e.g., acetate, formate, halide, or pentafluorobenzenesulfonate. The quaternary amine group in the carbene reagent can be a pyridinium ion. Cation-prone groups include picolinoyl, pyridinoyl, and 3-aminopyridyl groups.

In some embodiments, the diazirine is an ionic liquid.

In certain embodiments, the diazirine used in the methods of the present invention is

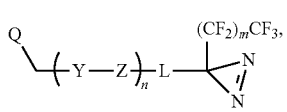

(I)

represented by formula (I):
wherein, independently for each occurrence,
Q is —NR$^6$R$^7$, —(NR$^6$R$^7$R$^8$)$^+$X$^-$, pyridyl, or

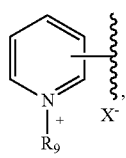

X is Hal, NO$_3$, OC(O)CH$_3$, OC(O)C(CH$_3$)$_3$, OC(O)CF$_3$, HCO$_3$, AsO$_2$, H$_2$AsO$_4$, AsF$_6$, SO$_3$(C$_4$F$_9$), SO$_3$(C$_6$F$_{13}$), SO$_3$C$_8$F$_{17}$, ClO$_4$, CN, BF$_4$, SnCl$_3$, CF$_3$SO$_3$, or C$_6$F$_5$O;
R$^6$, R$^7$, R$^8$ is each independently C$_{1-6}$ alkyl or C$_{6-10}$ aryl;
R$^9$ is C$_{1-3}$ alkyl;
Y is C$_{6-10}$ aryl or 5-membered to 9-membered heteroaryl;
Z is —(CH$_2$)$_l$A(CH$_2$)$_k$—;
L is —(CH$_2$)$_l$A(CH$_2$)$_k$— or absent;
A is O, S, or NH;
l is 0 to 2;
k is 0 to 2;
m is 0 to 10; and
n is 1 to 3.

In some embodiments, Q is —(NR$^6$R$^7$R$^8$)$^+$X$^-$ or —NR$^6$R$^7$. In some embodiments, Q is —(NR$^6$R$^7$R$^8$)$^+$X$^-$. In some embodiments, Q is —NR$^6$R$^7$. In some embodiments, Q is —(PR$^6$R$^7$R$^8$)$^+$X$^-$, pyridyl, or

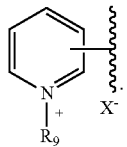

In some embodiments, pyridyl or

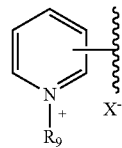

is substituted with one to two groups selected from C$_{1-3}$ alkyl and NH$_2$, or a combination thereof. In some embodiments, Q is —(PR$^6$R$^7$R$^8$)$^+$X$^-$.

In some embodiments, R$^6$, R$^7$, and R$^8$, if present, is each independently C$_{1-3}$ alkyl. In some embodiments, R$^6$, R$^7$, and R$^8$, if present, is each C$_2$ alkyl.

In some embodiments, X is Hal or OC(O)CH$_3$. In some embodiments, X is Hal. In some embodiments, X is F. In some embodiments, X is Cl. In some embodiments, X is Br. In some embodiments, X is OC(O)CH$_3$.

In some embodiments, Y is C$_{6-10}$ aryl. In some embodiments, Y is phenyl. In some embodiments, Y is 5-membered to 9-membered heteroaryl.

In some embodiments, one or more A is O. In some embodiments, one or more A is NH. In some embodiments, n is 3, at least one A is O, and at least one A is NH.

In some embodiments, L is —(CH$_2$)$_l$A(CH$_2$)$_k$—. In some embodiments, L absent.

In some embodiments, l is 0. In some embodiments, l is 1. In some embodiments, l is 2.

In some embodiments, k is 0. In some embodiments, k is 1. In some embodiments, k is 2.

In some embodiments, m is 0. In some embodiments, m is 1 to 3. In some embodiments, m is 1 to 3. In some embodiments, m is 1, 2, 3, 4, 5, 6, 7, 8, 9, or 10.

In certain embodiments, the diazirine is selected from the group consisting of

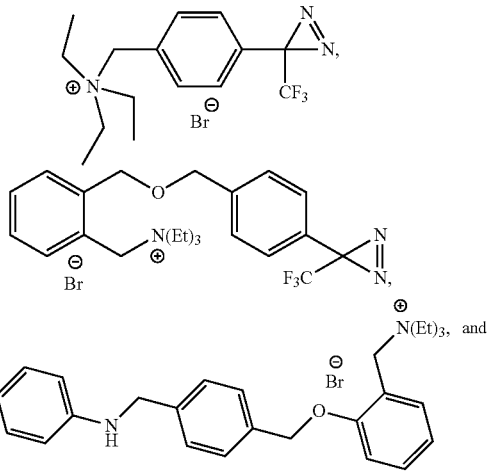

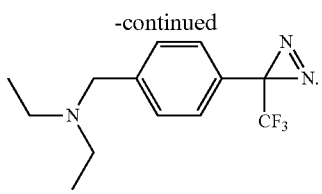

In certain preferred embodiments, the diazirine is

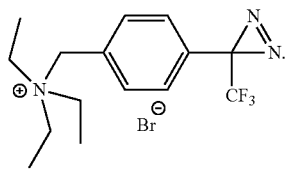 [SMILES: CC[N+](CC)(CC)Cc1ccc(C2(C(F)(F)F)N=N2)cc1 ; [Br-]]

In some embodiments, the material is a drug, metabolite, peptide, protein, lipid, glycan, or nucleic acid.

In other aspects, the invention provides a method of reacting a carbene, comprising the steps of:
(i) providing a solid comprising a first solid surface on which a diazirine is adsorbed;
(ii) exposing the diazirine to a source of energy, thereby generating a carbene and nitrogen gas;
wherein the nitrogen gas evolves from the first solid surface with sufficient energy to desorb the carbene from the first solid surface; and
(iii) reacting the desorbed carbene with one of:
   (a) a material in the gas phase proximal to the first solid surface;
   (b) a material adsorbed on a second solid surface proximal to the first solid surface, wherein the second solid surface is comprised by the solid or a second solid; or
   (c) a second solid surface proximal to the first solid surface, wherein the second solid surface is comprised by the solid or a second solid.

In certain embodiments, the desorbed carbene is in the gas phase. Alternatively, the carbene may be in the liquid phase.

In certain embodiments, the method comprises reacting the desorbed carbene with a material in the gas phase proximal to the first solid surface, thereby generating a labeled material.

In certain embodiments, the method comprises reacting the desorbed carbene with a material adsorbed on a second solid surface proximal to the first solid surface, wherein the second solid surface is comprised by the solid or a second solid. In alternative methods, the method comprises reacting the desorbed carbene with a second solid surface proximal to the first solid surface wherein the second solid surface is comprised by the solid or a second solid.

In certain embodiments, the source of energy is selected from the group consisting of UV photons, LED photons, UV LED photons, heat, laser photons, electrons, photons from fluorescence energy transfer, plasma, a metastable compound, an energy-releasing molecule, a vibrationally-activated molecule, and a combination thereof. The energy-releasing molecule may be, for example, ozone, an ozonide, or a peroxide. In some preferred embodiments, the source of energy is heat, a laser photon, or an LED photon.

In certain embodiments, the method further comprises analyzing the desorbed material. Analyzing the desorbed material may include, for example, analyzing the desorbed material by an analytical method selected from the group consisting of ion mobility spectrometry, mass spectrometry, liquid chromatography-electrospray ionization mass spectrometry, infusion-electrospray ionization mass spectrometry, laser desorption mass spectrometry, and matrix-assisted laser desorption ionization mass spectrometry. In preferred embodiments, the analytical method is ion mobility spectrometry, mass spectrometry, or laser desorption mass spectrometry, most preferably is laser desorption mass spectrometry.

In certain embodiments, the diazirine comprises a quaternary amine associated with a counterion, e.g., acetate, formate, halide, or pentafluorobenzenesulfonate.

In some embodiments, the diazirine is an ionic liquid.

In certain embodiments, the diazirine is selected from the group consisting of

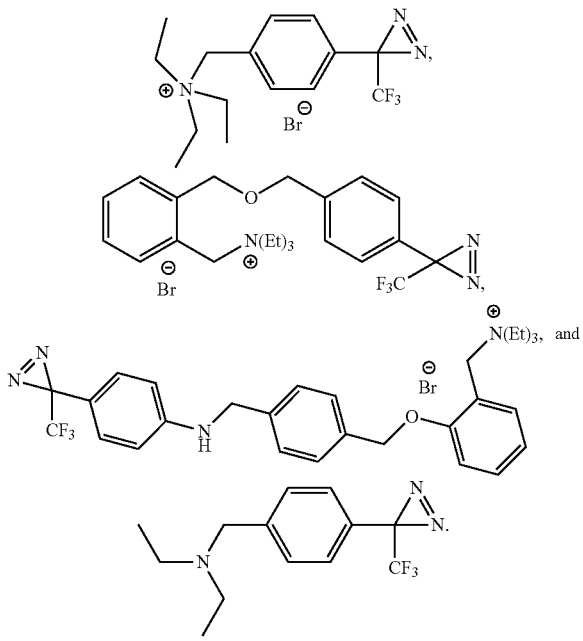

In certain preferred embodiments, the diazirine is

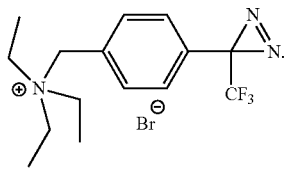 [SMILES: CC[N+](CC)(CC)Cc1ccc(C2(C(F)(F)F)N=N2)cc1 ; [Br-]]

The present invention takes advantage of the nitrogen released during energetic activation of a diazirine layer adsorbed on a solid surface, or of a layer having a diazirine adsorbed on a solid surface, to desorb an adsorbed or entrained material in or on the layer, or to desorb a carbene from a adsorbed, entrained, or covalently-attached diazirine of the layer. The released nitrogen can desorb one or more of the diazirine, a carbene from the diazirine (except when the diazirine is covalently attached to the solid surface or to the layer in the first place, prior to energetic activation), a second material, or a carbene conjugate of a second material, into a gas or vacuum phase above the surface. This can lead to several useful outcomes. In some embodiments, a third material already in the gas phase can be labeled by a gas phase carbene, as for synthesizing a fourth material of interest such as a new drug candidate. In some embodiments, a third material already in the gas phase can be labeled to help its detection by mass spectrometry or ion mobility mass spectrometry. In such a detection experiment, a third compound may also be present in the sample spot to help features such as enhanced harvesting of a photon, or to weaken the lattice of the spot. Examples of such a third compound are alpha-cyano-4-chlorocinnamic acid, 2-(4'-hydroxyazobenzene) benzoic acid, and an ionic liquid. In some embodiments, a novel material, or novel surface coating, can be formed on a second surface near the first surface. In other embodiments, the ability of a third material in the layer with the diazirine to be detected by mass spectrometry or ion mobility spectrometry can be improved via desorption as is, or after labeling with a carbene, especially with a mass tag carbene. In other embodiments, the method enables the new technique of "covalent modification atomic force microscopy". In some embodiments, subjecting a drug or drug candidate on a second surface to a gas phase carbene is a new way to construct a drug candidate library ("flash medicinal chemistry"). In some embodiments, the N2D2-MS method overcomes disadvantages of MALDI-MS, such as one or more of the following problems of MALDI-MS: limited scope, lack of ruggedness; too much tuning including searching for a hot spot to get a good result; difficult with quantitation; and a relatively large quantity of matrix in the MALDI spot. In N2D2-MS, far less diazirine can be used, relative to the typical amount of matrix in MALDI, to reduce background peaks, e.g. 100× less diazirine was present in the spot in FIG. 1 relative to the usual amount of matrix in a spot when MALDI is employed. In other embodiments, N2D2-MS, unlike MALDI, can provide "everything detection", that is, detection of all or nearly all of the organic chemicals in a sample via mass tag carbene labeling of the same. In further embodiments, a chelating diazirine can enable detection of metal ions in N2D2-MS. N2D2-MS is simple whereas MALDI-MS is complex. N2D2-MS and MALDI-MS can be combined by including a diazirine in a MALDI matrix to give a desorption performance that is greater than either one separately or greater than the sum of their individual performances.

In certain embodiments, the diazirine used in the methods of the invention is a quaternary amine diazirine. This is particularly preferred for N2D2-MS detection purposes.

In some embodiments, the diazirine is an ionic liquid.

In some embodiments, the diazirine is a quaternary amine diazirine having a counterion selected from formate, acetate, pentafluorobenzene sulfonate, trifluoroacetate, hexafluorophosphate, alpha-cyano-4-chlorocinnamate, alpha-cyano-4-hydroxy cinnamate; fluoride, and perfluorooctanesulfonate.

In certain embodiments relating to construction of a drug candidate library ("flash medicinal chemistry"), a great diversity of diazines have been synthesized, and many are available commercially. Of particular interest is a CAX-leash-diazirine, where the CAX group, having a positive charge, tends to make the CAX-leash-carbene label the drug only once due to charge repulsion, and the leash is cleavable, leading to modification of the drug at only one site with part of the leash. The labeling can be directed at one part of the drug by sequestering the remainder of the drug with a binding partner such as an aptamer. This invention can lead to high-speed proteomics, a subject of great interest, based on high throughput N2D2 desorbing intact proteins free of matrix and bearing a single charge, where they are desorbed initially as neutrals, and then application of the repeller voltage field removes a single counterion. The opportunity to minimize or avoid matrix (unlike MALDI), and to avoid contact of analyte with a hot metal surface (unlike SALDI) are major advantages of N2D2-MS Further Methods In a first embodiment of the invention, a diazirine, which comprises part of a layer on a first solid surface, is subjected to energy, thereby splitting the diazirine into a carbene and nitrogen gas. The carbene, assisted by the nitrogen, is desorbed from the surface for reaction with a material already present in a gas phase next to the surface, with a material on a second solid surface near the first surface, or with a second solid surface that is nearby. This embodiment is useful for labeling a compound of interest in the gas phase, and for probing or modifying the exposed structure of a material on a second surface. This embodiment is also useful for building or extending a molecular structure on a second surface via attachment of carbenes. The energy applied to create the carbene and nitrogen can comprise electrical, heat, laser photon, IR photon, LED photon, magnetron photon, or ultrasonic wave. In preferred embodiments, the energy is a photon with a wavelength near 350 nm. A major advantage is that carbenes are very reactive, so many different second solid surfaces and materials thereon can be modified. For example, consider an antibiotic which has lost its effectiveness. Placing the antibiotic on the second surface and subjecting it to "flash medicinal chemistry" by means of N2D2, where it is modified to give multiple products by reaction with carbene molecules desorbed by nitrogen from a first surface, can yield a compound with new potency against infections.

In a second embodiment of the invention, there is a layer on a solid surface, which layer comprises a diazirine and another material; where the other material can be part of the layer or on the surface of the layer; and the layer is subjected to energy, splitting the diazirine into a carbene and nitrogen gas. The carbene, assisted by the nitrogen, leaves the surface or layer in an relatively unreactive or inert form because of its rearrangement, its intramolecular-reactivity, or steric hindrance of its carbene moiety. This minimizes formation of carbene-labeled or carbene-modified material, effecting desorption of the other material of the layer for a purpose, such as detection or synthesis with minimal or no labeling of the same.

In a third embodiment, there is a layer on a solid surface, which layer comprises a diazirine and another material; wherein the diazirine is covalently attached to the solid surface or to the layer; and the layer is subjected to energy, splitting the diazirine into a carbene and nitrogen. There is no or negligible release of the carbene due to its covalent attachment to the surface or the layer. Instead, the released nitrogen desorbs the other material for the purpose of detection or synthesis. In certain embodiments, the material starts out adsorbed to the external surface of the layer, while the layer underneath comprises the diazirine.

In a fourth embodiment, a material of interest is detected by a gas phase method, wherein the material starts out on a first solid surface as part of a layer also containing a diazirine; the layer comprises a covalently-attached or non-covalently-incorporated diazirine; the layer is subjected to energy that reaches the diazirine; the diazirine splits to form a carbene and nitrogen; the nitrogen delivers or helps to deliver one or more of the diazirine, the carbene, the material, or a carbene-labeled material into the gas phase; and one or more of these species is detected. The energy source can be any source described above. In preferred embodiments, the energy is a photon with a wavelength near 350 nm. Preferred is detection by mass spectrometry or ion mobility spectrometry. Preferred is a quaternary amine diazirine with a counterion giving a weak ion pair (such as an acetate or formate counterion) with a low lattice energy, and where the material is converted into a quaternary amine-substituted material that is detected. Also preferred is a covalently-attached diazirine, leading to a desorbed material that is detected.

In another embodiment, a nonaqueous diazirine is adsorbed on a solid surface; the diazirine also is in contact with a liquid layer on the solid surface; energy is applied to desorb, with nitrogen assistance, the resulting carbene into the liquid; and the carbene reacts with a dissolved or undissolved substance in the liquid, or with an undissolved substance in contact with the liquid.

The solid surface supporting the diazirine can have a charge, as by imposing a voltage on it, or by the first surface being an electret, when the energy for desorption is applied. Numerous materials may be used as a solid first surface, having a wide variety of compositions and structures. Such first solid surfaces may include metals, plastics, glasses, silicas, silicones, organic polymers, organo-metallic polymers, carbons, ceramics, salts, alloys, woods, and rubbers. The first surface can vary from flat to rounded to a sharp tip. For example, the sharp tip of a probe used in atomic force microscopy can be employed to precisely modify a material of interest, such as a gene, protein, RNA, cell, virus, ribosome, organelle, or bacterium. The first solid surface can be smooth or rough or porous or nonporous. The first solid surface may be part of a fiber. The technology can be used to edit a gene in a way that avoids the side reaction problem of CRISPR. Molecules to be detected on a second surface can be derivatized by a carbene from a first surface, and then detected on the second surface by MALDI-MS. Preferred for this derivatization is a quaternary amine carbene. If a fluorescent carbene is used to label an adsorbed but soluble material of interest on a second solid surface, then detection can be achieved by dissolving the labeled substance and subjecting it to chromatography or electrophoresis, followed by fluorescence detection.

In some embodiments, the invention provides a method for covalently labeling a material with a carbene, wherein the material is present in a gas phase in contact with a first surface, consists of a second surface separated from the first surface by a gas phase, or consists of a material on a second surface separated from the first surface by a gas phase; a diazirine is present on the first surface; energy is applied to split the diazirine into a carbene and nitrogen gas; and the nitrogen delivers the carbene from the first surface to label the material.

In certain embodiments, the energy is provided by heat, a laser photon, or an LED photon.

In certain embodiments, the diazirine is a quaternary amine ion having a counterion. Exemplary counterions include acetate, formate, fluoride and pentafluorobenenesulfonate.

In certain embodiments, the layer comprises an ionic liquid.

In certain embodiments, the solid surface is glass, indium-tin-oxide coated glass, or gold coated glass.

In certain embodiments, the invention provides a method for detecting a material by a gas phase method, wherein the material starts out on or in a layer on a solid surface; the layer also comprises a diazirine; the diazirine receives energy which splits it into a carbene and nitrogen gas; the nitrogen delivers the material or a carbene-labeled targeted material into the gas phase; and one or both of these materials is detected.

In certain embodiments, the energy is provided by heat, a laser photon, or an LED photon.

In certain embodiments, the detection occurs by mass spectrometry or ion mobility spectrometry.

In certain embodiments, the diazirine is a quaternary amine ion (quaternary ammonium ion) having a counterion. Exemplary counterions include acetate, formate, fluoride and pentafluorobenenesulfonate.

In certain embodiments, the layer comprises an ionic liquid.

In certain embodiments, the layer comprises alpha-cyano-4-chlorocinnamic acid or alpha-cyano-4-hydroxycinnamic acid.

In certain embodiments, the diazirine is covalently attached to the solid surface or to the layer.

In certain embodiments, the material is a protein.

This invention provides a new, useful way to achieve modification of a second solid surface including the option of printing a precise structure on it. A nongaseous diazirine adsorbed on a first solid surface liberates a carbene via nitrogen assistance to modify a nearby second surface. A major advantage is that carbenes are very reactive, so many different second solid surfaces can be modified. Preferred is a nongaseous diazirine.

Materials and Methods

Compound CAX-DZ

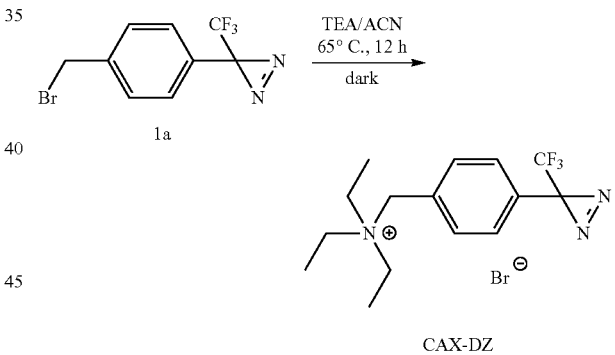

CAX-DZ

Compound 1a (10 mg, 0.0358 mmol) was placed in a 2 mL amber glass vial and dissolved in 400 µL of acetonitrile (ACN). Triethylamine (20 µL) was added to the mixture, the vial was closed and heated at 65° C. for 12 h in dark. The contents were allowed to cool to room temperature, and all volatiles were removed using vacuum. The residue was dissolved in 0.5 mL of ACN and loaded onto the OASIS™ HLB cartridge, which was allowed to dry for one hour. The cartridge was washed and eluted by applying the following sequence: 2 mL of 5% ACN in water; 3 mL of 20% ACN; 4 mL of 50% ACN; and 1 mL of 95% ACN. The last two fractions were combined and the volatiles were removed under vacuum to give compound CAX-DZ. The compound was stored in the dark at 4° C., and aliquots were taken and weighed to prepare stock solutions. This synthesis is described in International Patent Application, WO 2020/237132 A1, P. Kulkarni, R. Giese, P. Wang, Carbene Mass Tagging, Nov. 26, 2020 (incorporated by reference).

Acetate Salt of CAX-DZ

An aqueous solution of CAX-DZ bromide, prepared as described above, (2 mg/mL) was added to 1 mL of a solution of silver acetate in water (3 mg/mL). The solution was vortexed for 1 min and then centrifuged for 10 min at 13.5 g. The supernatant was transferred to a new vial followed by evaporation to dryness under vacuum. The dried residue was stored in an amber vial at 4° C. Other counterions such as fluoride, nitrate, trifluoroacetate, chloride, perfluorobutane sulfonate, perfluorohexane sulfonate, pentafluorophenolate, bicarbonate, or arsonate can be substituted similarly or by ion exchange chromatography of the CAX-DZ bromide.

Alpha-Cyano-4-Chlorocinnamate Salt of CAX-DZ

Alpha-cyano-4-chlorocinnamic acid is converted to a silver salt by reaction with silver acetate in water for 5 minutes. The intermediate product is isolated by chromatography (e.g. OASIS cartridge or RP-HPLC), reacted with CAX-DZ bromide as above, and purified as above to give the final product.

Alpha-Cyano-4-Hydroxycinnamate Salt of CAX-DZ

This compound is prepared in the same way as the alpha-cyano-4-chlorocinnamate salt of CAX-DZ except starting with alpha-cyano-4-hydroxycinnamic acid.

Pentafluorobenzene Sulfonate Salt of CAX-DZ

Pentafluorobenzene sulfonic acid is converted to a silver salt by reaction with silver acetate in water for 5 minutes. The intermediate product is isolated by chromatography and reacted with CAX-DZ bromide and purified as above to give the final product.

Conjugate of Alpha-Cyano-4-Hydroxycinnamic Acid Ethyl Ester (ACHCAEE) and 1-[4-(Bromomethyl)Phenyl]-1-Di-azirinyl-2,2,2-Trifluoro-Ethane (BPDTFE).

Alpha-cyano-4-hydroxycinnamic acid, an intense photon-absorbing compound, is converted to ACHCAEE with ethanolic HCl, and the ACHCAEE is coupled to BPDTFE in acetonitrile at 65° C. in the dark in the presence of triethylamine, to give an intense photon-absorbing conjugate product. This product is purified on an OASIS cartridge by applying in 5% acetonitrile; eluting with a step gradient of acetonitrile in water; and collecting the fractions containing product. This product is useful for enhanced desorption by nitrogen, since not only can the diazirine part absorb a photon, but the photon-absorbing part also can absorb a photon and pass it to the diazirine part. The latter pathway is especially powerful since the photon-absorbing part absorbs a photon very efficiently. A similar conjugate for the same purpose is prepared by substituting 2-(4'-hydroxyazobenzene) benzoic acid (also an intense photon absorber) for alpha-cyano-4-hydroxycinnamic acid. These diazirine conjugates therefore are especially powerful for practicing this invention because they are much better photon absorbers and thereby nitrogen-releasers than an ordinary diazirine.

Examples

Detection of Acebutolol by N2D2-MS

Five uL of CAX-DZ acetate in acetonitrile (0.2 mg/mL) was combined with 1 uL of acebutolol in acetonitrile (190 ug/mL) followed by addition of 95 uL of acetonitrile. After mixing, 0.2 uL was spotted onto a MALDI plate. After drying, laser desorption (frequency-tripled Nd:YAG laser on a SCIEX 5800 MALDI-TOF/TOF-Mass spectrometer) was done, giving the spectrum shown in FIG. 1. As seen, both a peak for acebutolol and CAX-acebutolol are observed.

Detection of Peptides by N2D2-MS

A tryptic digest of albumin is combined with CAX-DZ acetate followed by spotting onto a MALDI plate and then laser desorption and spectrum collection. Peaks are observed for CAX-labeled peptides.

Detection of Nucleic Acids by N2D2-MS

DNA is digested with a restriction enzyme and the resulting digest is combined with CAX-DZ acetate followed by spotting onto a MALDI plate and then laser desorption and spectrum collection. Peaks are observed for CAX-labeled DNA molecules. The experiment also is successful with CAX-DZ pentafluorophenylsulfonate.

Surface Modification with a Diazirine-Derived Carbene

A glass surface is coated noncovalently with a layer of phenyltrifluoromethyl diazirine in acetonitrile followed by evaporation. A polyethylene sheet is placed about 1 mm or less from this glass surface and the assembly is placed under vacuum or nitrogen. The back of the glass plate (side opposite the diazirine layer) is subject to UV radiation, or is heated with a hot air gun or an infrared lamp or a hot surface as from a hot plate. This coats the polyethylene surface with phenyltrifluoromethine groups. Other diazirines such as CAX-DZ acetate also can be used. Other surfaces can be coated in this way. If the glass is coated with a spot or a certain pattern of diazirine, the corresponding spot or pattern can be created on the second surface.

Tissue Imaging Using CAX-DZ Acetate

Figure 6:
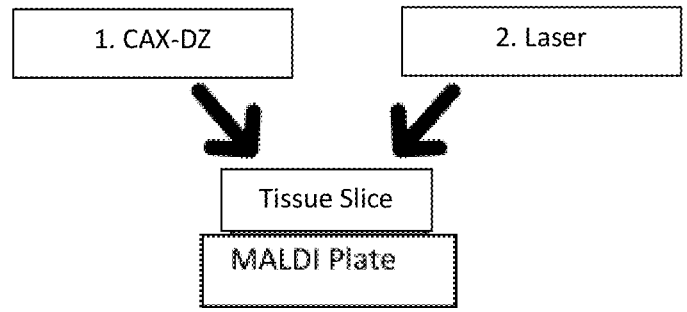
FIG. 6 shows a concept for N2D2-MS to enhance tissue imaging, wherein analytes in the tissue are first treated with CAX-DZ, and then upon being subjected to laser energy are simultaneously CAX-labeled and desorbed for detection by MS.

A slice of dried tissue on a MALDI target is imaged by applying CAX-DZ acetate followed by laser desorption mass spectrometry. See FIG. 6.

Desorption and Detection of DNA

A glass surface is reacted with aminopropyltriethoxysilane, giving a surface functionalized with aminopropyl groups. The surface is reacted with the N-hydroxysuccinimide ester of 4-(carboxy)phenyl-trifluoromethyl-diazirine, giving a covalentlyl-bound diazirine. Onto this surface a solution of DNA molecules up to a 1000-mer in an ammonium form is evaporated. The glass is mounted in the source of a MALDI mass spectrometer perpendicular to the repeller plate for detection by orthogonal TOF. Firing a frequency-tripled Nd:YAG laser at the plate releases nitrogen that in turn desorbs DNA molecules that are detected.

Gene Editing by Covalent Modification Atomic Force Microscopy

A sample of DNA containing a portion of interest, such as a gene to be deactivated, is deposited on a mica surface that has been coated with 3-aminopropyltriethoxy silane to fix the DNA. Fluorescent DNA probes that mark the ends of the gene are applied followed by washing away unbound probes. Using the AFM tip, or under fluorescent microscopy, the gene is located and an AFM tip containing an adsorbed diazirine is located over the gene. Subjecting the AFM tip to a burst of photons with a wavelength of about 350 nm, or heating the tip electrically, desorbs carbenes that covalently modify the targeted portion of the DNA.

N2D2-MS Peaks from an ITO Plate Subjected to a Diazirine Silanizing Reagent and Spotted with Acebutolol and Palmitoyl Carnitine An ITO slide from Hudson Technologies, after washing with water and acetonitrile, followed by drying with a Kimwipe, was cleaned further with an oxygen plasma (2 minutes, 100 watts). It was then reacted with 10% 3-(3-methyl-3H-diazirine-3-yl)-N-(3-(triethoxysilyl)propyl)propanamide (Sigma-Aldrich 907332) in the presence of 5% N-propylamine in toluene under two conditions: 1 h at 85° C. and 8 h at 85° C. in the dark, in an aluminum boat having an aluminum lid. The plates were washed with toluene, wiped with a Kimwipe and spotted with a 50% acetonitrile solution of acebutolol. A similar solution of palmitoyl carnitine was also spotted, and spots were made from the solvent as a control. The spots were dried in the dark, and then subjected to laser-desorption mass spectrometry-MS. The spots for acebutolol gave some unique peaks, as did the spots for palmitoyl carnitine.

Preparation of a Gold-Coated, Diazirine Plate Suitable for N2D2-MS.

A gold-coated slide from Hudson Surface Technology, after cleaning with aqua regia, is reacted with aminooctyl-thiol, followed by reaction with succinimidyl-4,4'-azipentanoate in phosphate buffer at pH 8.0.

Preparation of a Covalent Organic Framework Doped with a Polymeric Diazirine Suitable for N2D2-MS A thin film covalent organic framework (COF) is prepared on an ITO slide as described (Li, W., Wang, Q., Cui, J., Chou, H., Shaheen, S. E., Jabbour, G. E., Anderson, J., Lee, P., Kippelen, B., Peyghambarian, N., Armstrong, N. R., Marks, T. J. (1999) Covalently Interlinked Organic LED Transport Layers via Spin-Coating/Siloxane Condensation. Adv. Mater. 11, 730-374). A polymeric diazirine dopant is prepared by reacting succinimidyl-4,4'-azipentanoate with polyethyleneimine (PEI) in phosphate buffer at pH 8.0. The COF is treated with this polymeric diazirine dopant. This can be followed by cross-linking the embedded diazirine-PEI with adipic acid bis-NHS ester. Polyaniline can be used in place of PEI.

Preparation of a Gold-Coated Slide Coated with a Diazirine-Functionalized Polyamine Film for N2D2-MS A gold-coated glass slide is reacted with 3-mercaptopropionic acid as described (Du, X., Zhu, B-J., Chao, Z., Wang, C., Zhao, M-X. [2019] Polyamine-Modified Gold Nanoparticles Readily Adsorb on Cell Membranes for Bioimaging. ACS Omega 4, 17850-17856. This is followed by conversion of the carboxylic groups to NHS esters, for reaction polyethyenimine. Then succinimidyl-4,4'-azipentanoate is reacted with the polyethylenimine in phosphate buffer at pH 8.0.

Preparation of a Polyethylenimine Thin Film Having Covalently-Attached Diazirines on an ITO Slide for N2D2-MS A polyethyleneimine thin film is formed on an ITO slide by spraying as described (Falco, A., Zaidi, A. M., Lugli, P. Abdellah, A. [2015] Spray deposition of Polyethylenimine thin films for the fabrication of full-sprayed organic photodiodes. Organic Electrodes 23, 188-192. This is followed by reaction with succinimidyl-4,4'-azipentanoate in phosphate buffer at pH 8.0.

Preparation of a Porous Thin Film Incorporating a Diazirine Ionically.

A thin film with doped-in polystyrenesulfonic acid is prepared as described (Carter, S. A., Angelopouos, M., Karg, S., Brock, J., Scott, J. C. [1997] Polymeric anodes for improved polymer light-emitting diode performance. Appl. Phys. Lett. 70, 2067-2069), and treated with CAX-DZ.

Drug Delivery

The tip of a fiber optic cable, which may be an ITO-coated tip, is derivatized as in the above example "Preparation of a polyethylenimine thin film having covalently-attached diazirines on an ITO slide for N2D2-MS", and then coated with a drug by evaporation of a drop of a solution of the drug on the tip. In a biopsy procedure monitored by ultrasound, a needle with the fiber optic inside is brought to a tumor, and the fiber optic is extruded from the tip of the needle, and light is applied to the other end of the fiber optic to trigger N2D2 of the drug.

Nano/Micro 3D-Like Printing

A thin glass slide or ITO glass slide is derivatized as in the above example "Preparation of a polyethylenimine thin film having covalently-attached diazirines on an ITO slide for N2D2-MS", and then coated on this side (side A) with a material of interest, or various zones are coated with various materials. A pulse of photons delivered by a fiber optic to the other side (side B) desorbs some material from side A in a 3D-like process, but at the nano or micro scale to create a special tiny structure such as a molecular motor or a novel vehicle for drug delivery, assembled molecule by molecule. A special assembly of cells can be created in this way, for the purpose of precisely studying cell-cell interactions in mixtures.

Removal of a Protective Film.

A glass or ITO glass surface is partly derivatized as in the above example "Preparation of a polyethylenimine thin film having covalently-attached diazirines on an ITO slide for N2D2-MS", and partly with aminopropyltriethoxysilane. Antibodies are attached to the latter amino groups using glutaraldehyde. A protective plastic film is placed on the surface. When the surface is ready to be used for antibody based detection, the plastic film first is removed by N2D2.

What is claimed is:

1. A method of desorbing an adsorbed material, comprising the steps of:
   (i) providing a solid comprising a first solid surface on which a diazirine and a material are adsorbed;
   (ii) exposing the diazirine to a source of energy, thereby generating a carbene and nitrogen gas;
   wherein the nitrogen gas evolves from the first solid surface with sufficient energy to desorb the material from the first solid surface.

2. The method of claim 1, wherein the diazirine and the material are comprised in a single layer adsorbed on the first solid surface;
   optionally wherein the diazirine and the material are homogeneously distributed in the single layer; or
   optionally wherein the diazirine and the material are heterogeneously distributed in the single layer.

3. The method of claim 1, wherein the diazirine is comprised in a first layer adsorbed on the first solid surface, and the material is comprised in a second layer adsorbed on the surface of the first layer.

4. The method of claim 1, wherein the diazirine is covalently bound to the first solid surface.

5. The method of claim 1, wherein the carbene is not desorbed from the first solid surface.

6. The method of claim 1, wherein the diazirine is not covalently bound to the first solid surface.

7. The method of claim 1, wherein the carbene is desorbed from the first solid surface.

8. The method of claim 7, wherein the carbene is substantially inert.

9. The method of claim 1, wherein the carbene reacts with the material to form a labeled material in the gas phase after the material is desorbed from the first solid surface; or
   wherein the carbene reacts with the material to form a labeled material before the material is desorbed from the first solid surface.

10. The method of claim 1, wherein the source of energy is selected from the group consisting of UV photons, LED photons, UV LED photons, heat, laser photons, electrons, photons from fluorescence energy transfer, plasma, a metastable compound, an energy-releasing molecule, a vibrationally-activated molecule, and a combination thereof.

11. The method of claim 1, further comprising analyzing the desorbed material.

12. The method of claim 1, wherein the desorbed material reacts with a reagent;
  optionally wherein the desorbed material reacts with a reagent in the gas phase; or
  optionally wherein the reagent is bound to or adsorbed on a second solid surface, wherein the second solid surface is comprised by the solid or a second solid, and wherein the desorbed material reacts with a reagent on the second solid surface.

13. The method of claim 1, wherein the diazirine comprises a quaternary amine associated with a counterion.

14. The method of claim 1, wherein the material is a drug, metabolite, peptide, protein, lipid, glycan, or nucleic acid.

15. A method of reacting a carbene, comprising the steps of:
  (i) providing a solid comprising a first solid surface on which a diazirine is adsorbed;
  (ii) exposing the diazirine to a source of energy, thereby generating a carbene and nitrogen gas;
    wherein the nitrogen gas evolves from the first solid surface with sufficient energy to desorb the carbene from the first solid surface; and
  (iii) reacting the desorbed carbene with one of:
    (a) a material in the gas phase proximal to the first solid surface;
    (b) a material adsorbed on a second solid surface proximal to the first solid surface, wherein the second solid surface is comprised by the solid or a second solid; or
    (c) a second solid surface proximal to the first solid surface, wherein the second solid surface is comprised by the solid or a second solid.

16. The method of claim 15, wherein the desorbed carbene is in the gas phase or liquid phase.

17. The method of claim 15, wherein the method comprises reacting the desorbed carbene with a material in the gas phase proximal to the first solid surface, thereby generating a labeled material.

18. The method of claim 15, wherein the method comprises reacting the desorbed carbene with a material adsorbed on a second solid surface proximal to the first solid surface, wherein the second solid surface is comprised by the solid or a second solid.

19. The method of claim 15, wherein the method comprises reacting the desorbed carbene with a second solid surface proximal to the first solid surface, wherein the second solid surface is comprised by the solid or a second solid.

20. The method of claim 15, wherein the diazirine comprises a quaternary amine associated with a counterion.

* * * * *